United States Patent
Bly

(10) Patent No.: US 9,775,740 B2
(45) Date of Patent: *Oct. 3, 2017

(54) ASSEMBLY FOR TREATING AND PREVENTING MOISTURE RELATED SKIN DERMATITIS

(71) Applicant: Deborah C Bly, Chesterfield, MO (US)

(72) Inventor: Deborah C Bly, Chesterfield, MO (US)

(*) Notice: Subject to any disclaimer, the term of this patent is extended or adjusted under 35 U.S.C. 154(b) by 772 days.

This patent is subject to a terminal disclaimer.

(21) Appl. No.: 13/935,309

(22) Filed: Jul. 3, 2013

(65) Prior Publication Data
US 2013/0296980 A1 Nov. 7, 2013

Related U.S. Application Data

(63) Continuation of application No. 12/775,217, filed on May 6, 2010, now Pat. No. 8,480,724.

(60) Provisional application No. 61/175,983, filed on May 6, 2009.

(51) Int. Cl.
*A61F 7/00* (2006.01)

(52) U.S. Cl.
CPC ...... *A61F 7/0085* (2013.01); *A61F 2007/006* (2013.01); *A61F 2007/0078* (2013.01); *A61F 2007/0095* (2013.01)

(58) Field of Classification Search
CPC .................. A61F 7/85; A61F 2007/006; A61F 2007/0064
See application file for complete search history.

(56) References Cited

U.S. PATENT DOCUMENTS

| | | | |
|---|---|---|---|
| 3,947,659 A | 3/1976 | Ono | |
| 4,523,589 A * | 6/1985 | Krauser | A61M 15/00 128/203.27 |
| 4,602,146 A | 7/1986 | Barns et al. | |
| 4,699,136 A * | 10/1987 | Krauser | A61M 15/00 128/203.22 |
| 4,924,602 A | 5/1990 | Ohlsen | |
| 5,038,769 A * | 8/1991 | Krauser | A61M 15/00 128/203.27 |
| 5,144,757 A | 9/1992 | Sasso | |

(Continued)

FOREIGN PATENT DOCUMENTS

WO    WO 2008129357 A2 * 10/2008  ............. A61F 7/007

*Primary Examiner* — Kaitlyn Smith
(74) *Attorney, Agent, or Firm* — Polster Lieder

(57) ABSTRACT

An assembly for preventing and treating skin dermatitis includes an air flow conditioning module positioned in the output air flow increasing or decreasing the temperature of the generated air flow as received from the fan responsive to a received control signal, a temperature sensor positioned in the output air flow sensing a current temperature of the output air flow as conditioned by the air flow conditioning module, an air flow conditioning control module is coupled to the air flow conditioning module and the temperature sensor for generating the control signal, and air flow conditioning control module that has a definable temperature range of the output airflow and for receiving the sensed current temperature from the temperature sensor, comparing the current temperature to the defined temperature range, and generating the control signal to provide the generated air flow at the nozzle is within the defined temperature range.

20 Claims, 4 Drawing Sheets

(56) References Cited

U.S. PATENT DOCUMENTS

| | | | |
|---|---|---|---|
| 5,383,918 A * | 1/1995 | Panetta | A61F 7/0053 |
| | | | 607/104 |
| 5,420,961 A * | 5/1995 | Walker | A45D 44/00 |
| | | | 392/403 |
| 5,456,702 A * | 10/1995 | Falk | A61F 7/00 |
| | | | 600/549 |
| 5,459,944 A | 10/1995 | Tatsutani et al. | |
| 5,471,763 A | 12/1995 | McArthur | |
| 5,608,975 A | 3/1997 | Hsu | |
| 5,759,149 A * | 6/1998 | Goldberg | A61M 16/109 |
| | | | 600/22 |
| 5,790,749 A | 8/1998 | Polaert et al. | |
| 5,873,178 A | 2/1999 | Johnson | |
| 5,956,863 A | 9/1999 | Allen | |
| 6,026,821 A | 2/2000 | Last | |
| 6,216,363 B1 * | 4/2001 | Swansen | A47K 10/48 |
| | | | 34/415 |
| 6,718,651 B2 | 4/2004 | Perez et al. | |
| 6,766,589 B1 | 7/2004 | Bory et al. | |
| 7,913,416 B1 | 3/2011 | Scieri | |
| 9,463,124 B2 * | 10/2016 | Lachenbruch | A61G 7/001 |
| 2005/0101911 A1 * | 5/2005 | Chester | A61F 7/10 |
| | | | 604/113 |
| 2006/0216267 A1 | 9/2006 | Kovacs et al. | |
| 2006/0236557 A1 | 10/2006 | Bousfield | |
| 2008/0031924 A1 * | 2/2008 | Gilson | A61N 5/0616 |
| | | | 424/433 |
| 2008/0228247 A1 * | 9/2008 | Fung | A61F 7/007 |
| | | | 607/107 |
| 2008/0253984 A1 | 10/2008 | Kovacs et al. | |
| 2009/0312823 A1 * | 12/2009 | Patience | A61F 7/007 |
| | | | 607/104 |
| 2010/0095439 A1 * | 4/2010 | Nolan | A42B 3/286 |
| | | | 2/421 |
| 2010/0100090 A1 * | 4/2010 | Rose | A61F 7/10 |
| | | | 606/22 |
| 2010/0286754 A1 * | 11/2010 | Bly | A61F 7/0085 |
| | | | 607/107 |
| 2013/0013034 A1 * | 1/2013 | Quisenberry | A61B 18/203 |
| | | | 607/107 |
| 2014/0343639 A1 * | 11/2014 | Hopper | A61F 7/0085 |
| | | | 607/104 |
| 2015/0313354 A1 * | 11/2015 | Mongan | A47K 7/02 |
| | | | 15/22.1 |
| 2015/0320592 A1 * | 11/2015 | Black | A61F 7/12 |
| | | | 607/105 |

* cited by examiner

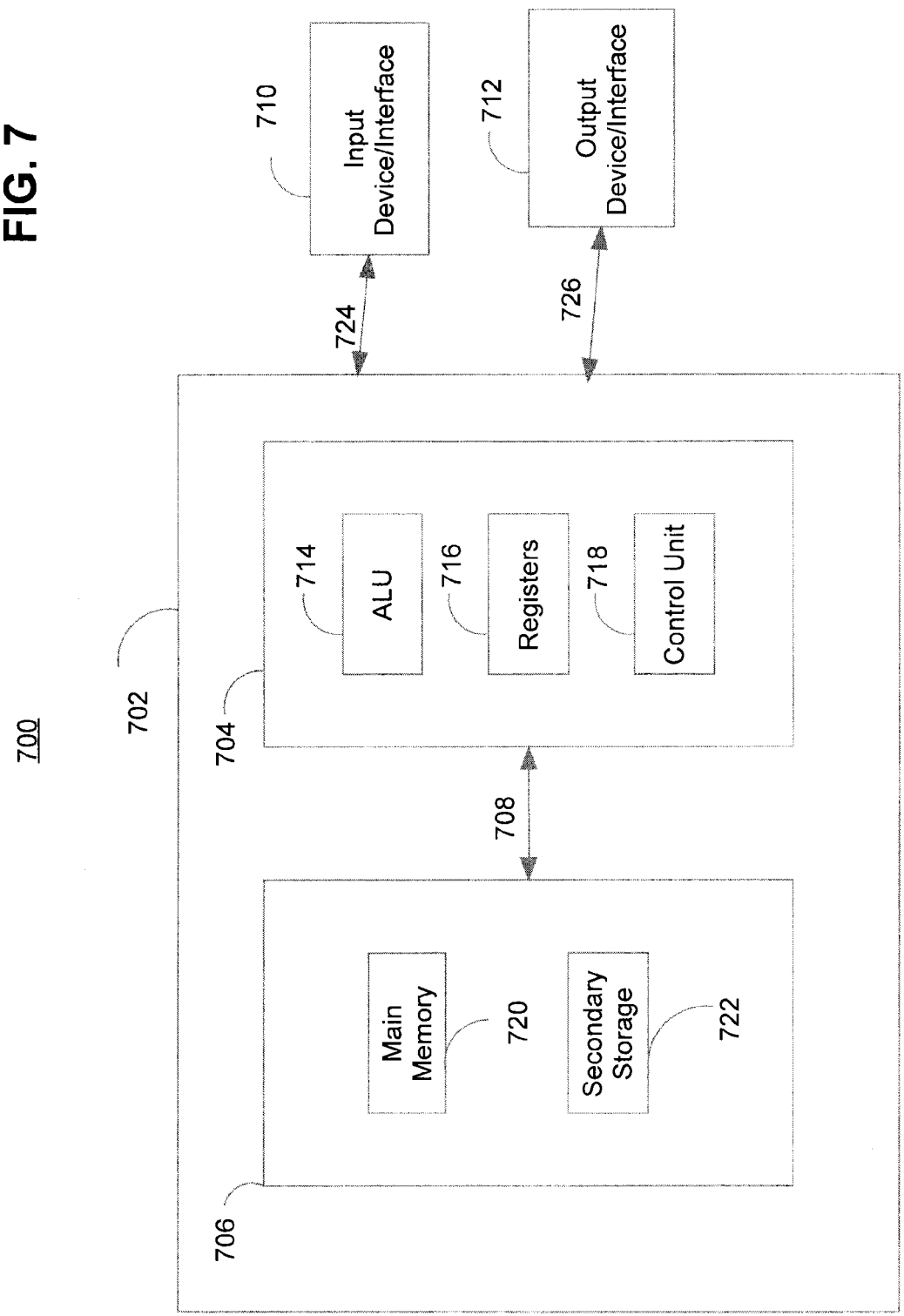

ASSEMBLY FOR TREATING AND PREVENTING MOISTURE RELATED SKIN DERMATITIS

CROSS-REFERENCE TO RELATED APPLICATIONS

This application is a continuation application of U.S. patent application Ser. No. 12/775,217, which is now U.S. Pat. No. 8,480,724, issued Jul. 9, 2013, which claimed the benefit of U.S. Provisional Application No. 61/175,983 filed on May 6, 2009, each of which are herein incorporated by reference.

FIELD

The present disclosure relates to an assembly for a clinical condition and, more specifically, to an assembly for treating and preventing moisture related skin dermatitis caused by excessive exposure to moisture on the skin of a patient.

BACKGROUND

The statements in this section merely provide background information related to the present disclosure and may not constitute prior art.

Dermatitis can be an acute or chronic inflammation of the skin. There are a multitude of causal agents. Some causes include but are not limited to chemical irritants, allergic reactions, genetic conditions, infectious processes and excessive moisture. These causal events are immediately followed by the necessary reaction of the body, resulting in an interplay of actions and events aiming at restoration of the skin to its original state. In the case of skin related dermatitis, excessive contact with moisture can soften the layer of strength at the epidermal layer that can soften the skin and disrupt the integrity of the multiple protective layers of the skin. For example, this can result in possibly negatively affecting the dermal-epidermal junction with the constant effects of maceration, and as a result weakening the integrity of the skin and its underlying strengthening components. When skin integrity is broken the underlying basic protective modalities from invasion of pathogens is compromised. Further, with the moisture that builds up in skin folds the normal skin Ph is altered causing a negative affect on the inherent antibacterial protective mechanisms. Lower or higher Ph values can allow pathogens to proliferate in this warm moist environment. When skin becomes macerated with constant moisture and integrity of the protective layers of the skin are broken, a portal of entry for bacteria can be created that potentiates the risk of infection at a tissue level. In the debilitated individual this type of infection can lead to sepsis. Bacteria, either as a primary causal agent or during a secondary infection, can damage the surrounding tissue as well. Often negative reactions are kept at bay by application of bacteria inhibitors. The inventor hereof has found that maintaining skin integrity is paramount in preventing this pathway. Constant moisture causing maceration should be eliminated. Many medications and personal care items have been developed in order to remedy the severely itchy and often painful consequences of dermatitis. With severe dermatitis there is often impairment of the integumentary system decreasing the capability of this organ and its functions. The risk of infection to the host is increased with the interruption of the natural barrier-skin. Increased moisture in the intertriginous and other areas of the skin can increase skin vulnerability to dermatitis caused by moisture macerating effects to the layers of the epidermis and dermis, ultimately compromising the skin's integrity. Impaired integrity and moisture can lead to an increased risk of dermatitis and potentiate invasion of pathogens. In general, treatment of underlying causes will facilitate healing of dermatitis. General anti-inflammatory therapy and antibiotics are often chosen as treatments. Other ways of treating moisture-based dermatitis are mainly based on providing either a protective layer to the skin, e.g., by applying a lipid-based ointment containing additives such as zinc, or by frequently cleaning an area at risk. Special personal care items are endless. They have been developed, varying from specific wet wipes, absorbing discs, stoma rinsing fluids and creating protective layers with ointments.

However, these treatments typically can only alleviate one or more of the clinical symptoms from dermatitis. The inventor hereof has found that the elimination or reduction in moisture induced dermatitis would help eliminate the underlying cause. Presently all treatment modalities start by washing and drying skin. Complete drying of skin, especially in the intertriginous areas (such as skin folds), is often difficult. The disclosure hereof provides for prevention of moisture-based dermatitis and provides an adjunct therapy to other customary treatments. In some cases, relieving the skin completely free of moisture, Candidiasis and other opportunistic infections can be reduced. The warm moist environment that is conducive for their proliferation can be interrupted. Therefore, this disclosure can provide for decreasing moisture related dermatitis and its pathway of infection.

SUMMARY

As addressed herein, the Applicant has developed an assembly for preventing and treating moisture related skin dermatitis that is applicable for both a health care facility as well as home use.

In one aspect, an assembly for preventing and treating moisture-based skin dermatitis including a housing including a handle for grasping by the user, a motor positioned within the housing and a user control for receiving a user command and for controlling activation of the motor in response to a received user command. The assembly including a fan coupled to the motor for rotating and generating air flow under pressure, an input air flow chamber for drawing air from outside the housing to the fan, an output air flow chamber for receiving pressurized air from the fan, and a nozzle coupled to the output air flow chamber defining an air outflow port for directing the pressurized air flow from the output air flow chamber onto a treatment area of a patient's skin. The assembly also including an air flow conditioning module positioned in the output air flow in the output air flow chamber for increasing or decreasing the temperature of the generated air flow as received from the fan responsive to a received control signal. A first temperature sensor is positioned proximate to the output air flow sensing a current temperature of the output air flow as conditioned by the air flow conditioning module and a second temperature sensor is positioned proximate to the input air flow chamber sensing a current temperature of the air drawn from the outside to the fan. An air flow conditioning control module is coupled to the air flow conditioning module and the temperature sensors and generating the control signal, the air flow conditioning control module including a definable temperature range of the output airflow wherein the air flow conditioning control module is adapted for receiving the sensed current first and second temperatures from the temperature sensors, comparing the current temperature to the defined temperature range, and generating the control signal to provide the generated air flow at the nozzle is within the defined temperature range.

In yet another aspect, an assembly for preventing and treating moisture-based skin dermatitis is provided that has a housing including a handle for grasping by the user, a motor positioned within the housing, a fan coupled to the motor for rotating and generating air flow under pressure, a user control for receiving a user command and for controlling activation of the motor in response to a received user command, an input air flow chamber for drawing air from outside the housing to the fan, an output air flow chamber for receiving pressurized air from the fan, a nozzle coupled to the output air flow chamber defining an air outflow port for directing the pressurized air flow from the output air flow chamber onto a treatment area of a patient's skin. An air flow conditioning module is positioned in the output air flow in the output air flow chamber, the air flow conditioning module including a heating element for increasing the temperature of the generated air flow as received from the fan responsive to a received control signal. A temperature sensor is positioned proximate to the output air flow for sensing a current temperature of the output air flow as conditioned by the air flow conditioning module. A moisture sensor detects a moisture level of the air flow. An air flow conditioning control module is coupled to the air flow conditioning module and the temperature sensor, the moisture sensor, and the air flow conditioning module. The control module generates the control signal as a function of a definable temperature range and moisture range of the output airflow and responsive to receiving the sensed current temperatures from the temperature sensors and the sensed detected moisture level. The control module generating the control signal as a function of the comparing the sensed current temperatures to a current defined temperature range and the detected moisture level to a definable moisture range. The control module generates the control signal to provide that it is within the defined temperature range and within the defined moisture range.

In still another aspect, an assembly for preventing and treating moisture-based skin dermatitis having a housing including a handle for grasping by the user, a motor positioned within the housing, a fan coupled to the motor for rotating and generating air flow under pressure, a user control for receiving a user command and for controlling activation of the motor in response to a received user command, an input air flow chamber for drawing air from outside the housing to the fan, an output air flow chamber for receiving pressurized air from the fan, a nozzle coupled to the output air flow chamber defining an air outflow port for directing the pressurized air flow from the output air flow chamber onto a treatment area of a patient's skin. The assembly includes means for controlling a temperature range of the pressurized air flow through the nozzle and means for controlling a moisture range of the pressurized air flow through the nozzle.

Further aspects of the present disclosure will be in part apparent and in part pointed out below. It should be understood that various aspects of the disclosure may be implemented individually or in combination with one another. It should also be understood that the detailed description and drawings, while indicating certain exemplary embodiments, are intended for purposes of illustration only and should not be construed as limiting the scope of the disclosure.

BRIEF DESCRIPTION OF THE DRAWINGS

FIG. 7 is a block diagram of a computer system that can be used to implement an air flow conditioning module according to one exemplary embodiment.

It should be understood that throughout the drawings, corresponding reference numerals indicate like or corresponding parts and features.

DETAILED DESCRIPTION

Figure 1:
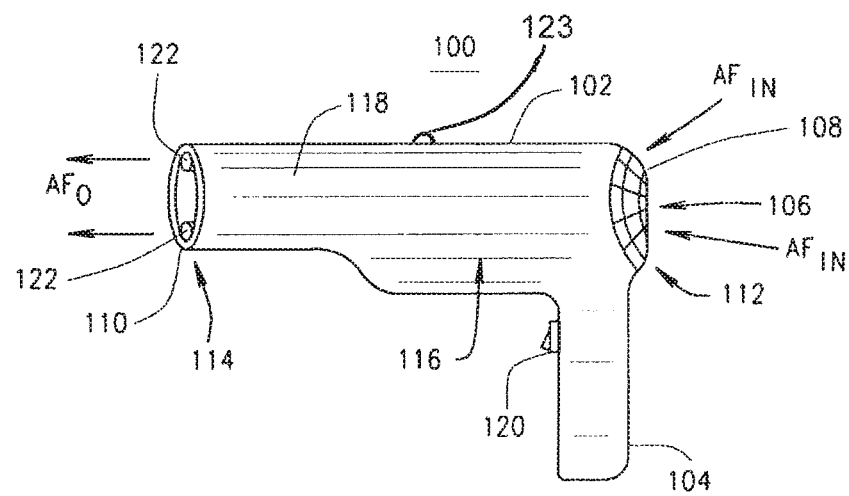
FIG. 1 is a side perspective view of an assembly for preventing and treating skin moisture created skin dermatitis according to one exemplary embodiment.

The following description is merely exemplary in nature and is not intended to limit the present disclosure or the disclosure's applications or uses.

Before turning to the figures and the various exemplary embodiments illustrated therein, a detailed overview of various embodiments and aspects is provided for purposes of breadth of scope, context, clarity, and completeness.

In one embodiment, an assembly for preventing and treating moisture-based skin dermatitis includes a housing including a handle for grasping by the user and a power source within the housing for providing self-contained electrical power to the assembly. A motor is positioned within the housing and a user control provides for receiving a user command and for controlling activation of the motor in response to a received user command. A fan is coupled to the motor for rotating and generating air flow under pressure. An input air flow chamber provides for drawing air from outside the housing to the fan and an output air flow chamber provides for receiving pressurized air from the fan. A nozzle is coupled to the output air flow chamber defining an air outflow port for directing the pressurized air flow from the output air flow chamber onto a treatment area of a patient's skin. An air flow conditioning module is positioned in the output air flow in the output air flow chamber for increasing or decreasing the temperature of the generated air flow as received from the fan responsive to a received control signal. A temperature sensor is positioned in the output air flow at the nozzle for sensing a current temperature of the output air flow as conditioned by the air flow conditioning module. An air flow conditioning control module is coupled to the air flow conditioning module and the temperature sensor and is configured for generating the control signal. The air flow conditioning control module includes a defined temperature that is a typically a maximum temperature of the output airflow. In some embodiments, the defined temperature is less than or equal to the temperature of the skin of the patient's body. This can be 98.6 degrees Fahrenheit, or can be set at a temperature less than 98.6, or another temperature. This can also include a range of temperatures The air flow conditioning control module is adapted for receiving the sensed current temperature from the temperature sensor, comparing the current temperature to the defined maximum temperature, and generating the control signal to provide the generated air flow at the nozzle does not exceed the defined maximum temperature.

In another embodiment, an assembly for preventing and treating moisture-based skin dermatitis includes a housing having a handle for grasping by the user, a motor positioned within the housing, a fan coupled to the motor for rotating and generating air flow under pressure, and a user control for receiving a user command and for controlling activation of the motor in response to a received user command. An input air flow chamber provides for drawing air from outside the housing to the fan and an output air flow chamber provides for receiving pressurized air from the fan. A nozzle is coupled to the output air flow chamber defining an air outflow port for directing the pressurized air flow from the output air flow chamber onto a treatment area of a patient's skin. A power source is positioned within the housing for providing self-contained electrical power to the assembly. A splash guard mounting fixture is positioned on an outer portion of the nozzle adapted for selectively attaching a disposable splash guard in a position for preventing the passing of moisture from beyond the nozzle in the direction of the handle. The mounting fixture can be any suitable for attaching a temporarily placed splash guard and can include, but is not limited to, clips, hook and loop material, extensions from the housing including a bridge radial extension of the body, by ways of examples.

An air flow conditioning module is positioned in the output air flow in the output air flow chamber. This air flow conditioning module includes a heating element for increasing the temperature of the generated air flow as received from the fan responsive to a received control signal. One or more temperature sensors are positioned in the output air flow at the nozzle. Each sensor provides for sensing a current temperature of the output air flow as conditioned by the air flow conditioning module. An air flow conditioning control module is coupled to the air flow conditioning module and each of the temperature sensors. The air flow conditioning module receives the current temperature from each of the temperature sensors and generates the control signal responsive thereto. The air flow conditioning control module includes a defined maximum temperature of the output airflow. The air flow conditioning control module is adapted for comparing the sensed current temperature to the defined maximum temperature, and generating the control signal to provide the generated air flow at the nozzle does not exceed the defined maximum temperature.

Referring now to the figures, an assembly 100 has a housing 102 that includes a handle 104 for grasping by a user and a cavity 106. The housing 102 is dimensioned and the cavity 106 is sized to encapsulate the working components of the assembly and to protect those components from outside interference. The housing 102 can be made of any suitable material and in one embodiment is a molded plastic. The handle 104 can be of any form on the housing 102 such as, for example, a pistol grip configuration, or otherwise that provides for ease of use by the users in directing airflow from the assembly 100. The housing 102 can include an airflow intake port 108 for receiving air into the cavity 106 and an airflow output port 110. As shown, the airflow intake port 108 can be positioned at a proximal end 112 with the airflow output port 110 positioned at an opposing distal end 114. However, it should be understood to those of skill in the art that the positioning of the airflow output port 110 could also be along a side 116 of the housing 102 as well. A nozzle 118 is defined by the housing 102 to include the output port 110 for directing output airflow. The user of the assembly 100 can direct the output airflow by directly the nozzle 118 at an area to be treated on the skin of a patient.

A user control 120 is provided for receiving the user selection input as to placing the assembly 100 in an on mode or an off mode. One or more temperature sensors 122 are positioned at the distal end 114 of the housing 102 such as at an end of the nozzle 118 or about the airflow output port 110.

Figure 2:
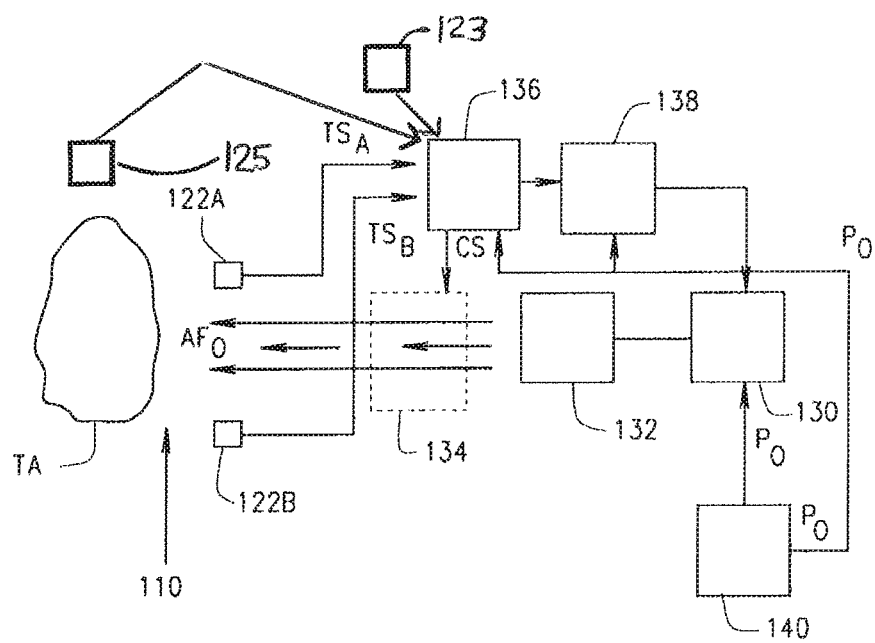
FIG. 2 is a block diagram of a control circuit for an assembly according to one exemplary embodiment.

As shown in FIG. 2, within the cavity 106 of the housing 102 the assembly 100 includes a motor 130 that drives a fan 132. As the motor 130 operates, the fan 132 rotates and pulls air into the cavity 106 through the airflow intake port 108 and generates output air flow that is under pressure or pressurized. The amount of the pressure of the output air flow depends on various factors as known to those of skill in the art including the rotational speed of the motor 130 and the design of the fan 132. The pressurized output airflow is directed by the nozzle 118 through the output airflow port 110 and by the temperature sensors 122 (shown in FIG. 2 as 122A, 122B). The temperature sensors 122 (shown as 122A and 122B) generate temperature signal TS (shown as TSA and TSB, respectively) that are representative of the sensed current temperature of the output airflow at the output airflow port 110. These sensors 122 can also be calibrated to estimate the temperature of the output airflow at the surface of a treatment area TA based on a sensing of the ambient temperature about the assembly 100 or the nozzle 118 via ambient temperature sensors 123 or a sensing of a temperature at or on the treatment area TA via treatment area sensors 125. Additional temperature sensors 125 can also be provided that sense the temperature at or on the treatment area TA and provide a separate signal back such as TTA.

An airflow conditioning module 134 is positioned in the output airflow from the fan 132 and typically is in the cavity 106 between the fan 132 and the airflow output port 110, such as within or proximate to the nozzle 118. The airflow conditioning module 134 provide for increasing and/or decreasing the temperature of the output airflow that passes by or through the airflow conditioning module 134 from the fan 132 to the output airflow port 110.

A control module 136, such as a control circuit or control processor is provided for controlling various aspects of the assembly 100 and is configured to receive the temperature signals $TS_A$ and/or $TS_B$. This can include controlling the rotational speed of the motor 130 and/or controlling the airflow conditioning module 134 to condition the airflow such as to increase or decrease the temperature as conditioned by the airflow conditioning module 134. As will be discussed other inputs and outputs are also possible by the control module.

In some embodiments, the motor 130 driving the fan 132 is a fixed speed motor 130 but in other embodiments, the motor 130 can have multiple user selectable speeds or even a variable speed wherein the user can select one of multiple speeds for adjusting the output air flow. In some embodiments, an air flow motor control module 138 is operatively coupled to the motor 130 or can be integrated within the functions of the control module 136 for controlling the speed of rotation of the motor 130.

A power source 140 provides power $P_O$ to each of the electrical components of the assembly 100. This includes the motor 130, the control module 136 and the motor control module 138. The power source 140 can be any type of power source or supply and $P_O$ can include both alternating current (AC) and direct current (DC). In some embodiments, the power supply 140. The power source 140 can be a replaceable battery, or can be a rechargeable battery energy source so that the assembly 100 can be operated in a cordless manner. In the later embodiment, a separate power supply or source or charger can be provided for charging and recharging the rechargeable battery energy source of the assembly.

Figure 3:
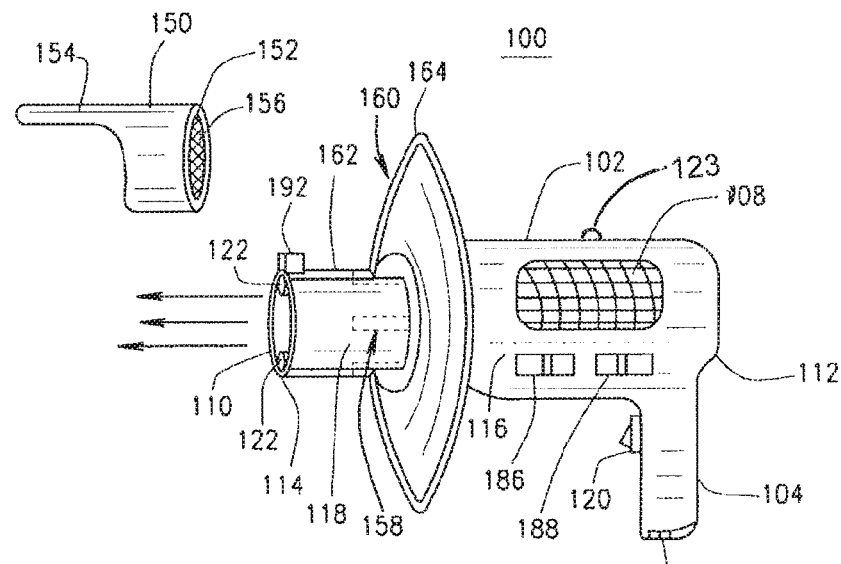
FIG. 3 is a side perspective view of an assembly for preventing and treating skin moisture created skin dermatitis according to a second exemplary embodiment.
Figure 4:
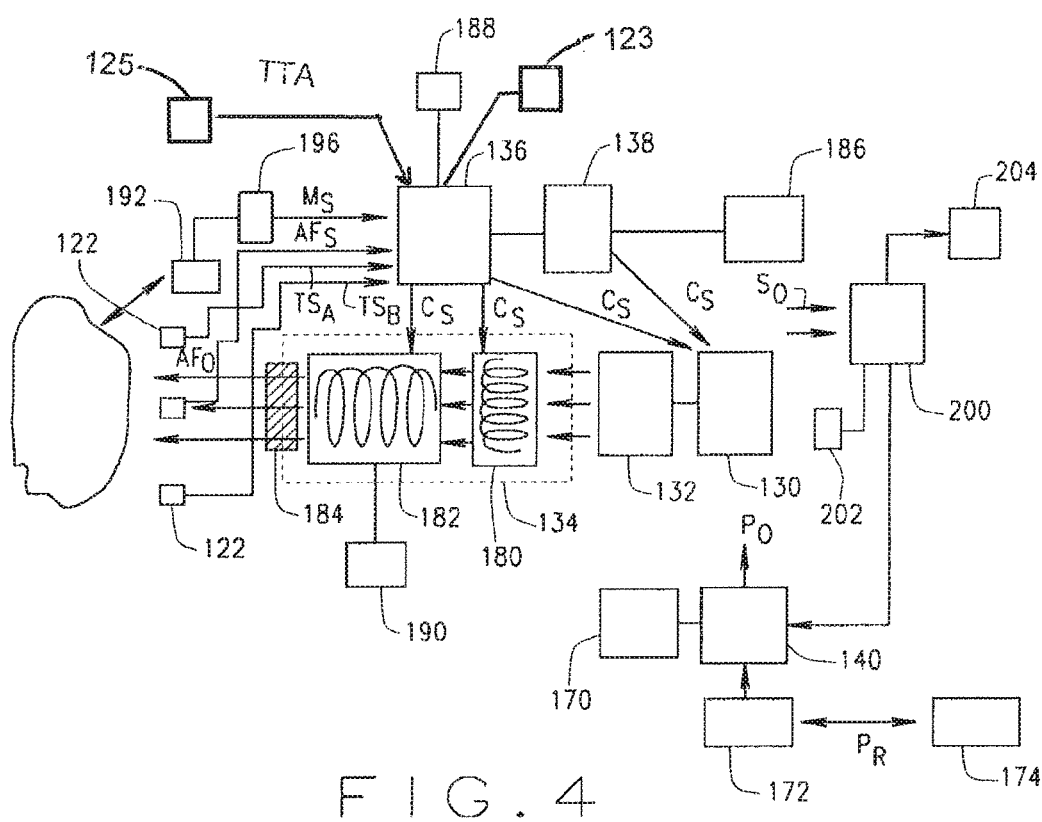
FIG. 4 is a block diagram of a control circuit for an assembly according to another exemplary embodiment.

FIGS. 3 and 4 illustrate additional embodiments and embodiment features of the assembly 100. As shown in FIG. 3, the intake airflow port 108 can be located, at least in part, on the side 116 of the housing 102. An integrated or detachable air deflector 150 that includes an attachment interface 152 for coupling to the nozzle 118 can provide for deflecting the output airflow. The air deflector 150 (can also be an air shaper) can include a partial deflector extension 154 that restricts or shapes the airflow in a particular direction. Additionally, the air deflector 150 can include an air diffuser 156 within the airflow path for diffusing the received airflow and providing a less direct airflow at its opposing end.

The housing 102, such as about the nozzle 118 can include a splash guard mounting fixture 158 for receiving and selectively securing a disposable splash guard 160. The mounting fixture 158 can be any suitable for attaching a temporarily placed splash guard 160 and can include, but is not limited to, clips, hook and loop material, extensions from the housing 102. This can also include a bridge or radial extension of the body that can provide structural support a radially extending splash guard 160 such as shown in FIG. 3 for example.

The disposable splash guard 160 can be of any type or shape or dimensions but can include a nozzle portion 162 for temporarily covering a portion of the nozzle 118. The splash guard 160 can be fixable about the output airflow port 110 or nozzle 118 that can be applied immediately prior to use on a particular patient and that is disposable after use with the particular patient. The disposability of splash guard 160 can help to ensure the cleanliness of the assembly 100 and can prevent the transmission of diseases between patients within a medical care facility. Additionally, the disposable splash guard 160 can include a radial or substantially perpendicular extension portion 164 that extends from the nozzle 118 or the housing 102 at an extended distance for limiting the passing of any debris or fluids from about the distal end 114, such as from the treatment area TA, to beyond the splash guard 160. As such, the splash guard 160 can be dimensioned and configured for providing a temporary shield to the assembly 100 as well as the user of the assembly 100 during its use.

Referring now to FIG. 4, in some embodiments the power source 140 providing the operating power PO can include a battery 170, which can be a replaceable or rechargeable battery. When a rechargeable battery is provided, the assembly 100 can include a powering or recharging interface 172 for receiving a recharging power PR from a recharging source or charging station 174.

As noted earlier, the airflow conditioning module 134 can provide for increasing or decreasing the temperature of the output airflow as received from the fan 132. As shown in FIG. 2, a cooling element 180 can be provided that reduces the temperature of airflow, such as a refrigeration element, by way of example. Such unit can also be utilized to decrease or remove humidity from the airflow that can aid in the drying of the treatment area TA. A heating element 182 can provide for heating or increasing the temperature of the output airflow. Any conditioning element of the airflow conditioning module 134 receives power from the power source 140 directly or indirectly and receives control signals $C_S$ from the control module 136.

An internal integrated diffuser 184 can also be provided within the cavity 106 and within the output airflow between the fan 132 and the output airflow port 110 for diffusing the airflow to equalize the airflow and pressure of the airflow across the output airflow port 110.

The air flow motor control module 138 can include a user airflow speed selection input 186 for receiving a user selection of the speed of the motor 130 and therefore selecting the air flow pressure and/or velocity and quantity of the output airflow. Additionally, a user selectable temperature input 188 can be provided for receiving a user selection of a temperature that would act as the defined temperature. The user selection is provided to the control module 136 for controlling the airflow conditioning module 134 and in some embodiments, controlling the speed of the motor 130. In some embodiments, the airflow conditioning module 134 can include a separate conditioning control module 190, or such functionality can be provided in whole or in part by the control module 136, such as with the motor control module 138.

Figure 5:
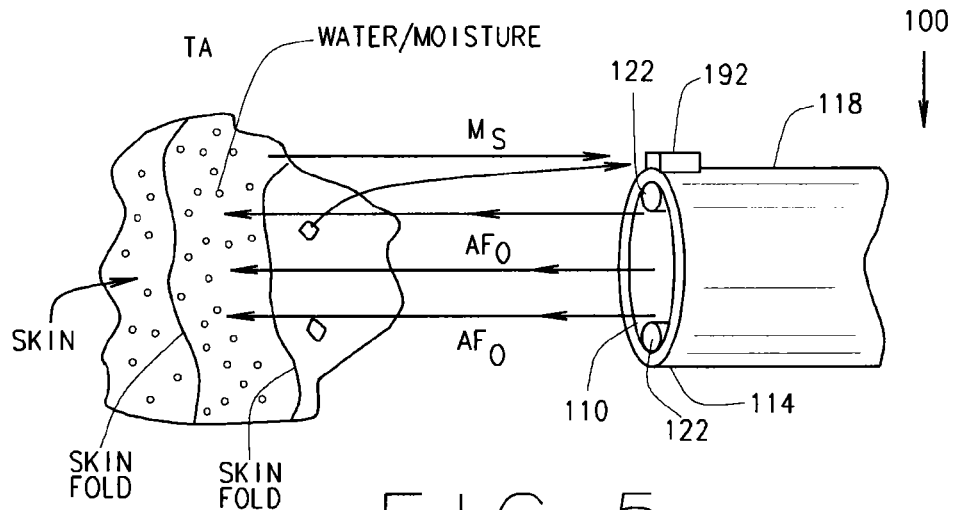
FIG. 5 is an illustration of a use of an assembly on a patient according to one exemplary embodiment.

A moisture sensor 192 can be placed proximate to the distal end 114 and configured for detecting a quantity or amount of moisture on the treatment area TA. The moisture sensor 192 can be any type of sensor capable of detecting an amount of moisture present on the skin of the treatment area, such as an infrared or LED light source and corresponding light collector or similar sensor as known to those skilled in the art of electronic moisture sensors. A moisture module 196 can be coupled to the moisture sensor 192 for receiving a detected moisture level or the control module 136 can provide this functionality. The moisture module 196 evaluates the signal received from the moisture sensor 192 and evaluates the actual moisture content as illustrated in FIG. 5. The moisture module 196 can include a user indicator such as a light or meter that provides the user with an indication of the moisture content of the skin of the treatment area TA. The sensed moisture $M_S$ is provided as a signal or message from the moisture sensor 192 to the control module 136. In this manner, the control module 136 can adjust or modify the control signals $C_S$ for adapting the airflow conditioning of the airflow by the airflow conditioning module 134 or adapting the speed of the motor 130 to account for that status or change of status of conditions on or at the treatment area TA. Additionally, when no more moisture is detected, the control module 136 can be configured to remove power from the fan 132 to prevent use where not required. As will be discussed, the sensed moisture can also be transmitted to a cut-off assembly 200 as will be discussed below.

In some embodiments, the defined temperature is less than or equal to the temperature of the skin of the patient's body. This can be 98.6 degrees Fahrenheit. In other embodiments the defined temperature is set to be less than or equal to an actual measurement of the temperature of the patient's skin at that time of the treatment. The temperature of the patient's skin being treated can be measured and then the user can set or input that temperature through the user selectable temperature input 188 to set the defined temperature for that treatment. The air flow conditioning module 134 using the inputs received directly or indirectly from the temperature sensors 122 as well as any other sensors (as will be discussed) can provide for the airflow at the treatment area TA that is as desired for the treatment, is safe for the patient, and that can be adapted to take into account differences in the patients and treatments.

Additionally, in some embodiments, the assembly 100 includes a safety cut-off module 200 for providing an override function to the operations of the assembly 100. The safety cut-off module 200 is configured to monitor the operations of the various elements, modules and functions of the assembly 100 to ensure their proper operation. Additionally, the safety cut-off module 200 can receive the sensed current temperatures $TS_A$ and/or $TS_B$ for detecting if and when the sensed current temperatures $TS_A$ and/or $TS_B$ exceed the defined temperature. When the safety cut-off module 200 detects a situation such as a failure of a sensor 122 or the sensed current temperature $TS_A$ and/or $TS_B$ exceeding the predefined temperature or the lack of moisture being detected on the treatment area TA by the moisture sensor 192, the control module 136 or the airflow conditioning module 134, the safety cut-off module 200 can be configured to remove power $P_O$ from the assembly and in some embodiments remove or disconnect the power $P_O$ from the fan 132 and/or the airflow conditioning module 134. This can also include providing an indication or indicator to the user that a fault of event has occurred such as the lighting of a light or an indicator indicating the fault or the type of fault. Additionally, the safety cut-off module 200 can be coupled to a fluid sensor 202 that is located on the housing 102 for detecting contact of the housing 102 with a liquid or fluid, such as water, or wherein the assembly has a potential situation for being electrically shorted. An indicator 204 can also provide a visual indication of such fault.

Figure 6:
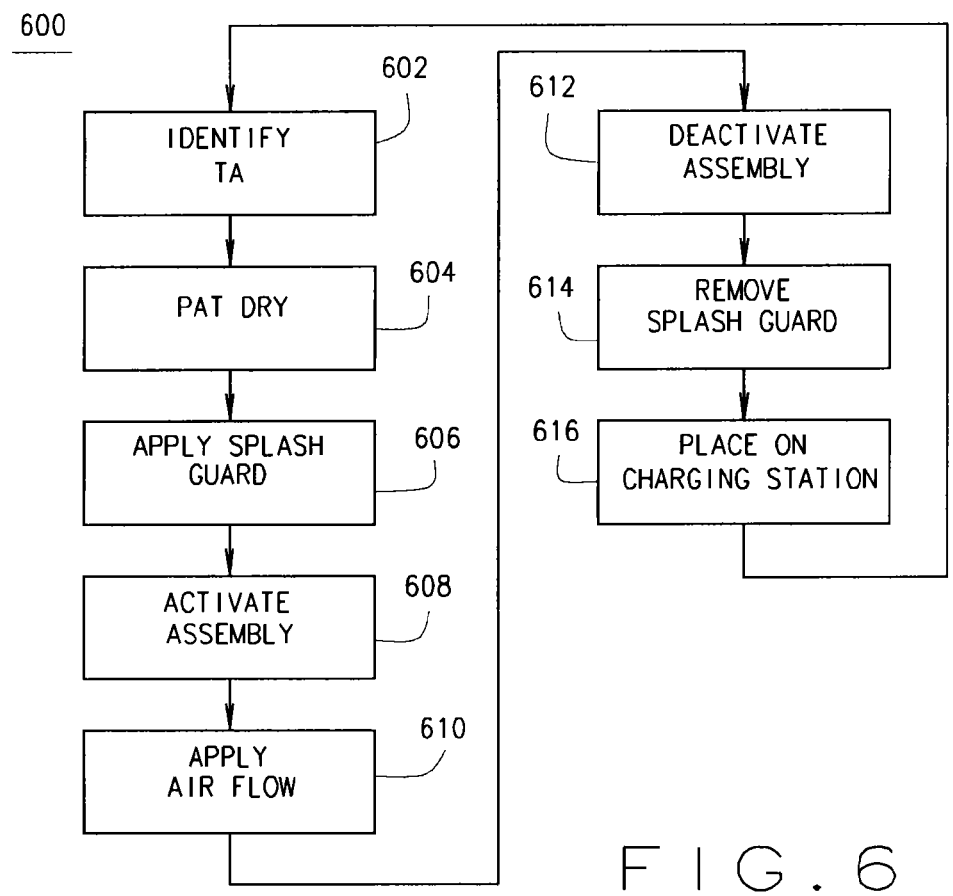
FIG. 6 is a block flow diagram of processes using an assembly for preventing and treating skin moisture-based skin dermatitis according to one exemplary embodiment.

In some embodiments, a method for preventing and treating moisture-based skin dermatitis using a noncontact normothermic air flow generating assembly such as shown in process 600 of FIG. 6 includes identifying a target treatment area 602, patting dry the skin surface within the target treatment area using a disposable absorbing material 604 and applying a splash guard 606. The next step is activating the assembly 608 at a desired output air flow and temperature. The method also includes applying a normothermic air flow 610 to the skin surface of the target treatment area until the surface of the skin is visually free of moisture. The assembly is deactivated in 612, the splash guard is removed in 614 and the assembly is placed on a charging station 616 for charging for the next use.

Referring now to FIG. 7, an operating environment for one or more illustrated embodiments of the control module 136 as described above can include a computer or processing system 700 having a computer 702 that comprises at least one high speed processing unit (CPU) 704, in conjunction with a memory system 706 interconnected with at least one bus structure 708, an input device 710, and an output device 712. These elements are interconnected by at least one bus structure 712. Examples of power control systems having one or more of these exemplary operating environment components, can include the power controllers, the local and remote user interfaces, the gateway, the operations system, and the remote operational system, by way of example.

The illustrated CPU 704 is of familiar design and includes an arithmetic logic unit (ALU) 714 for performing computations, a collection of registers 716 for temporary storage of data and instructions, and a control unit 718 for controlling operation of the system 700. Any of a variety of processor, including at least those from Digital Equipment, Sun, MIPS, Motorola/Freescale, NEC, Intel, Cyrix, AMD, HP, and Nexgen, is equally preferred for the CPU 704. The illustrated embodiment of the disclosure operates on an operating system designed to be portable to any of these processing platforms.

The memory system 706 generally includes high-speed main memory 720 in the form of a medium such as random access memory (RAM) and read only memory (ROM) semiconductor devices, and secondary storage 722 in the form of long term storage mediums such as floppy disks, hard disks, tape, CD-ROM, flash memory, etc. and other devices that store data using electrical, magnetic, optical or other recording media. The main memory 720 also can include video display memory for displaying images through a display device. Those skilled in the art will recognize that the memory system 706 can comprise a variety of alternative components having a variety of storage capacities.

The input device 710 and output device 712 are also familiar and can be implemented associated with the local and remote user interfaces as well as a controller, remote operational system and operations system, by way of example. The input device 710 can comprise a keyboard, a mouse, a physical transducer (e.g. a microphone), etc. and is interconnected to the computer 702 via an input interface 724. The output device 712 can comprise a display, an indicator light or audio device, a printer, a transducer (e.g. a speaker), etc, and be interconnected to the computer 702 via an output interface 726. Some devices, such as a network adapter or a modem, can be used as input and/or output devices.

As is familiar to those skilled in the art, the computer system 700 further includes an operating system and at least one application program. The operating system is the set of software which controls the computer system's operation and the allocation of resources. The application program is the set of software that performs a task desired by the user, using computer resources made available through the operating system. Both are resident in the illustrated memory system 706. As known to those skilled in the art, some of the methods, processes, and/or functions described herein can be implemented as software and stored on various types of computer readable medium as computer executable instructions. In various embodiments of the power control system described by example herein, the controller can include a robust operating and application program having the computer executable instructions for controlling the controller and the controlled devices. Additionally, one or more of the local and remote user interfaces, operations system and remote operations system can include, among other application software programs with computer executable instructions, a thin client application for communicating and interactively operating with one or more controllers as described above by way of example.

In accordance with the practices of persons skilled in the art of computer programming, the present disclosure is described below with reference to symbolic representations of operations that are performed by the computer system 700. Such operations are sometimes referred to as being computer-executed. It will be appreciated that the operations which are symbolically represented include the manipulation by the CPU 704 of electrical signals representing data bits and the maintenance of data bits at memory locations in the memory system 706, as well as other processing of signals. The memory locations where data bits are maintained are physical locations that have particular electrical, magnetic, or optical properties corresponding to the data bits. The disclosure can be implemented in a program or programs, comprising a series of instructions stored on a computer-readable medium. The computer-readable medium can be any of the devices, or a combination of the devices, described above in connection with the memory system 706.

As described herein, the assembly is suitable as an adjunctive therapy for preventing and treating moisture related/ based skin dermatitis by providing a noncontact, normothermic drying air flow to the skin of the patient. One exemplary embodiment of the use of the assembly 100 is shown in FIGS. 5 and 6. The assembly 100 can be used for drying a patient's skin to reduce the moisture content on the skin, to a greater degree than merely patting of the skin with an absorbing material. In particular, the assembly 100 can be used to evaporate selected undesirable moisture in the folds of the skin of a patient that are not otherwise easily treated both as a preventive process and as a treatment process after moisture related skin dermatitis has been identified as shown in FIG. 5 by way of illustration. The assembly 100 can be utilized until the affected area visually changes from a red to a pink coloration, in some cases. The following will describe some exemplary embodiments of processes using the assembly as described above.

The skin of a patient to be treated, i.e., the target treatment area, is identified. Any wounds in the target treatment area are covered to protect the wound base from undesired drying or moisture evaporation. All skin-based medicaments such as creams are removed from the target treatment area. This is advised as any skin medicaments such as creams can prevent the skin from drying and can in some cases heat at a greater temperature than the skin surface itself. The medical practitioner and possibly the patient should apply protective wear to their hands and eyes to prevent exposure from deflected moisture caused by the use of the assembly. A disposable splash guard 160 (also can be referred to as a splash shield) is applied to the assembly 100 to maintain a sterile housing 102 of the assembly 100 and prevent deflected moisture from contacting a surface of the housing 102. The splash guard 160 is applied during use and discarded after use for each patient. The target treatment area is patted dry with an absorbing material which is typically then discarded as well.

The assembly 100 is held in a single hand by the medical practitioner and activated to the desired output air flow and temperature for use. The assembly 100 is directed at the target treatment area indirectly or at an angle and is applied in a swinging or constantly moving manner over the skin. The assembly nozzle 118 is directed at the target treatment area but away from the medical practitioner and away from any vital areas of the patient at a predetermined distance such as 12 inches. The frequency and amount of time of use of the assembly 100 for each target treatment area can be adjusted by the medical practitioner to meet the needs of the patient. As noted above, the process using the assembly 100 can be repeated or continued until the target treatment area visually changes from red to pink. After use for the particular patient, the splash guard 160 is removed and the assembly 100 placed on a provided recharging source 174 or charger 174 as can be applicable for some embodiments of the assembly 100.

In some embodiments, the assembly 100 and its use as described herein provides for the more complete drying of skin that can prevent and treat moisture driven dermatitis. The assembly 100 can be used in adjunct therapy and is not intended to dismiss any medically prescribed treatments. In some embodiments, the assembly and method are to be used with mild to moderate moisture induced dermatitis. Their use is cautioned where wound beds exist or to clear secretions or dry a wound bed. Care should be taken to never over dry the skin such as granulation and/or epithelialized tissue. If skin condition worsens or does not improve, use of the assembly and method should be terminated and medical assistance should be sought.

Protective eye wear can be worn especially where a concern for the spreading of any infectious secretions. Universal safety precautions are always to be practiced by all personnel assisting with the procedure.

Where available, the defined temperature should be set to the desired level as a predefined temperature or selectable within a predefined range by the user. Such a normothermic temperature as provided by the assembly 100 will allow the skin surface to be dried without concern of burning of the skin surface. The rechargeable power source 140 can provide for increased safety especially in the presence of use around water. The assembly 100, as an electrical device, should not be immersed in water. After use the splash guard 160 should be discarded or cleansed with hospital regulated cleansing agents. The splash guard 160 should not be cleaned while attached to the assembly or when the assembly 100 is plugged into an AC outlet or on a charging station 174 or recharging source 174 or other energy source.

As noted, some of the embodiments of the assembly 100 as described herein and the methods of use can be used to prevent and/or treat moisture related skin dermatitis by removing undesired moisture from the skin using a noncontact normothermic assembly. Additionally, as described herein, embodiments of the assembly 100 include features that help to provide for the safe use of the assembly by medical practitioners.

It should be understood to those skilled in the art, that some embodiments of systems or components described herein may have more or fewer computer processing system components and still be within the scope of the present disclosure.

When describing elements or features and/or embodiments thereof, the articles "a", "an", "the", and "said" are intended to mean that there are one or more of the elements or features. The terms "comprising", "including", and "having" are intended to be inclusive and mean that there may be additional elements or features beyond those specifically described.

Those skilled in the art will recognize that various changes can be made to the exemplary embodiments and implementations described above without departing from the scope of the disclosure. Accordingly, all matter contained in the above description or shown in the accompanying drawings should be interpreted as illustrative and not in a limiting sense.

It is further to be understood that the processes or steps described herein are not to be construed as necessarily requiring their performance in the particular order discussed or illustrated. It is also to be understood that additional or alternative processes or steps may be employed.

What is claimed is:

1. An assembly for preventing and treating moisture-based skin dermatitis on a treatment area of a patient, the assembly comprising:
   a power source;
   a housing including a handle for grasping by the user;
   a motor positioned within the housing;
   a user interface for receiving a user command and for controlling activation of the motor and an air flow conditioning control module in response to a received user command;
   a fan coupled to the motor for rotating and generating air flow under pressure;
   an input air flow chamber for drawing air from outside the housing to the fan;
   an output air flow chamber for receiving pressurized air from the fan, a nozzle coupled to the output air flow chamber, the nozzle defining an air outflow port for directing the pressurized air flow from the output air flow chamber onto the treatment area of the patient's skin;

an air flow conditioning module positioned in output air flow for increasing and decreasing the temperature of the generated air flow as received from the fan responsive to a received control signal from the air flow conditioning control module;

a temperature sensor positioned proximate to the output air flow for sensing a current temperature of the output air flow as conditioned by the air flow conditioning module and generating a current output airflow temperature value, a moisture sensor positioned proximate to a distal end of the nozzle for detecting a quantity of moisture on the treatment area and coupled to the air flow conditioning control module, the moisture sensor generating the detected moisture quantity value;

a second temperature sensor sensing at least one of a current temperature of ambient air about the assembly and a current temperature at or on the treatment area, the second temperature sensor generating a current second temperature value; and the air flow conditioning control module coupled to the air flow conditioning module, coupled to the temperature sensor for receiving the generated current temperature value, coupled to the second temperature sensor for receiving the generated current secondary temperature value, and coupled to the moisture sensor for receiving the generated detected moisture quantity value, the air flow conditioning control module generating the control signal, the air flow conditioning control module including a definable temperature range of the output airflow wherein the air flow conditioning control module is adapted for receiving the sensed current temperatures from the temperature sensors, comparing the current temperatures to the defined temperature range, and generating the control signal to provide the generated air flow at the nozzle within the defined temperature range, the air flow conditioning control module further adapted for comparing the received detected treatment area moisture quantity value to a predefined moisture level and generating a control signal to the air flow conditioning module responsive to the comparison of the detected treatment area moisture quantity value to the predefined moisture level.

2. The assembly of claim 1, further comprising:
a splash guard mounting fixture positioned on an outer portion of the nozzle; and
a disposable splash guard selectively attachable to the splash guard mounting fixture for positioning relative to the nozzle for preventing the passing of moisture from beyond the splash guard in the direction of the handle.

3. The assembly of claim 1,
wherein the power source is within the housing for providing self-contained electrical power to the assembly, the self-contained power source being selected from the group consisting of a replaceable battery and a rechargeable battery energy source.

4. The assembly of claim 1 wherein the air flow conditioning module includes a heating element for increasing the temperature of the air flow responsive to the temperature of the control signal and a cooling module for lowering the temperature of the air flow responsive to the temperature control signal.

5. The assembly of claim 1, further comprising an automatic override module configured to provide at least one of a fault indicator on the user interface or a disablement of the motor responsive to a failure of at least one of the sensor, the air flow conditioning module, and the air flow conditioning control module.

6. The assembly of claim 1, further comprising a safety cut-off having a fluid sensor for sensing a contact of the housing with a conducting fluid, wherein the power source is isolated or disengaged from the other components of the assembly by the safety cut-off responsive to the fluid sensor.

7. The assembly of claim 6 wherein the safety cut-off is further configured for receiving the detected moisture quantify value from the moisture sensor and wherein the safety cut-off is responsive to the detected moisture quantity value at or on the treatment area.

8. The assembly of claim 1, further comprising an air flow deflector selectively attachable to the nozzle and configured for shaping of the airflow in a particular direction.

9. The assembly of claim 8, wherein the selectably attachable air flow deflector includes an air diffuser positioned within the airflow deflector and configured for providing a less direct airflow.

10. The assembly of claim 1 wherein the moisture sensor is selected from the group consisting of an infrared sensor, and an LED light source and light collector sensor.

11. The assembly of claim 1 wherein the user interface includes a moisture content indicator providing the user with an indication of the moisture level of the treatment area as detected by the moisture sensor.

12. The assembly of claim 1 wherein the air flow conditioning control module is configured to determine from the moisture sensor that there is no moisture on the treatment area and in response the air flow conditioning control module turns off the motor.

13. An assembly for preventing and treating moisture-based skin dermatitis having a housing including a handle for grasping by the user, a power source, a motor positioned within the housing, a fan coupled to the motor for rotating and generating air flow under pressure, a user interface for receiving a user command and for controlling activation of the motor in response to a received user command, an input air flow chamber for drawing air from outside the housing to the fan, an output air flow chamber for receiving pressurized air from the fan, a nozzle coupled to the output air flow chamber defining an air outflow port for directing the pressurized air flow from the output air flow chamber onto a treatment area of a patient's skin, the assembly comprising:

an air flow conditioning module positioned in the output air flow, the air flow conditioning module including a heating element for increasing the temperature of the generated air flow as received from the fan responsive to a received control signal;

a temperature sensor positioned proximate to the output air flow, the temperature sensor sensing a current temperature of the output air flow as conditioned by the air flow conditioning module;

a moisture sensor detecting a moisture level on the treatment area; and an air flow conditioning control module coupled to the air flow conditioning module, the temperature sensor and the moisture sensor, and the air flow conditioning module, the air flow conditioning control module generating the control signal, the air flow conditioning control module including a definable temperature range of the output airflow and moisture level of the treatment area responsive to receiving the sensed current temperatures from the temperature sensor and detected moisture level of the output air flow, comparing the sensed current temperature to the defined temperature range and the detected moisture level to the definable moisture level, and generating the control signal to provide the generated air flow at the nozzle within the defined temperature range.

14. The assembly of claim 13, further comprising a splash guard mounting fixture positioned on an outer portion of the nozzle and a splash guard selectively attachable to the splash guard mounting fixture for positioning relative to the nozzle for preventing the passing of moisture from beyond the splash guard in the direction of the handle.

15. The assembly of claim 13, wherein the power source is within the housing for providing self-contained electrical power to the assembly, the self-contained power source is a rechargeable battery energy source, further comprising a detached power source configured for charging and recharging the rechargeable battery energy source of the assembly.

16. The assembly of claim 13 wherein the air flow conditioning module includes a cooling element for lowering the temperature of the air flow responsive to the temperature control signal.

17. The assembly of claim 13, further comprising an automatic override module configured to provide at least one of a fault indicator and a disablement of the motor responsive to a detected failure of at least one of the temperature sensor and the moisture sensor, the air flow conditioning module, and the air flow conditioning control module.

18. The assembly of claim 13, further comprising a safety cut-off having a fluid sensor for sensing a contact of the housing with a conducting fluid, wherein the power source is isolated or disengaged from the other components of the assembly by the safety cut-off responsive to the fluid sensor.

19. The assembly of claim 1 wherein the second temperature sensor is configured for sensing the current temperature at or on the treatment area and wherein the air flow conditioning control module is configured for generating the control signal based on a comparison of the current temperature of the airflow to the current temperature at or on the treatment area.

20. The assembly of claim 1 wherein the motor is a variable speed motor and wherein the air flow conditioning control module generates a motor control signal for controlling the rotational speed of the motor and the motor is responsive to the generated motor control signal.

* * * * *